United States Patent [19]

Ashby et al.

[11] Patent Number: 5,630,819
[45] Date of Patent: May 20, 1997

[54] ACETABULAR BONE GRAFT IMPACTOR

[75] Inventors: Alan Ashby, Caen, France; Denis Pichon, Middlesex, England; Tom J. Slooff, Westerbeek, Netherlands

[73] Assignee: Howmedica International, Shannon, Ireland

[21] Appl. No.: 510,576

[22] Filed: Aug. 2, 1995

[30] Foreign Application Priority Data

Aug. 11, 1994 [GB] United Kingdom ............. 9416215

[51] Int. Cl.⁶ ........................................ A61B 17/00
[52] U.S. Cl. .......................... 606/81; 606/86; 606/91
[58] Field of Search .......................... 606/81, 86, 91, 606/92, 93, 94, 99, 100

[56] References Cited

U.S. PATENT DOCUMENTS

| 4,433,686 | 2/1984 | Charnley | 606/81 |
| 4,904,265 | 2/1990 | MacCollum | 623/22 |
| 5,116,339 | 5/1992 | Glock | 606/81 |
| 5,462,548 | 10/1995 | Pappas et al. | 606/81 |

FOREIGN PATENT DOCUMENTS

| 357270A | 3/1990 | European Pat. Off. . |
| 535973A | 4/1993 | European Pat. Off. . |
| 2233972 | 1/1975 | France . |
| 8623700 | 11/1986 | Germany . |
| 8605384 | 9/1986 | WIPO . |

*Primary Examiner*—Michael Powell Buiz
*Assistant Examiner*—Kevin Truong
*Attorney, Agent, or Firm*—Peter C. Richardson; Lawrence C. Akers; Raymond W. Augustin

[57] ABSTRACT

An acetabular bone graft impactor comprising a contact surface at least part of which is located on a head connected to a shaft provided with and anvil to be hit with a hammer. A flange extends from the head so that the contact surface shape can be selectively altered.

2 Claims, 4 Drawing Sheets

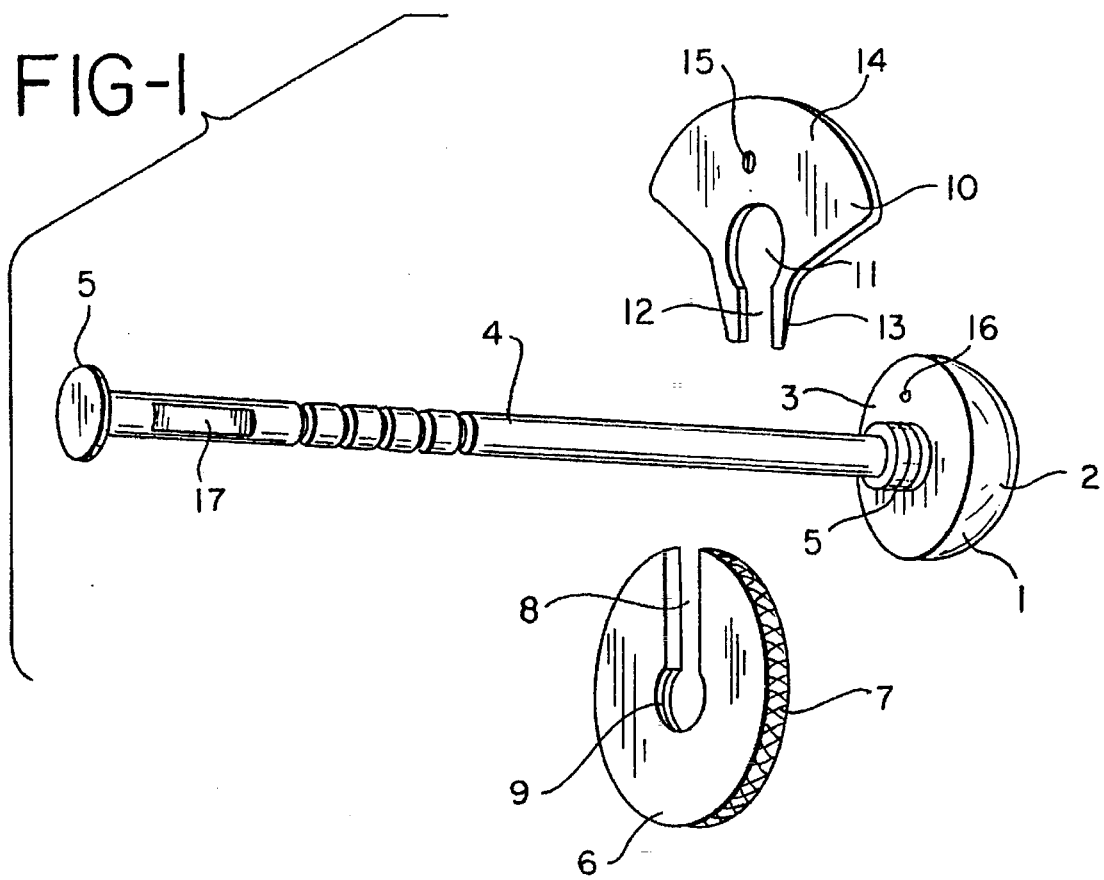
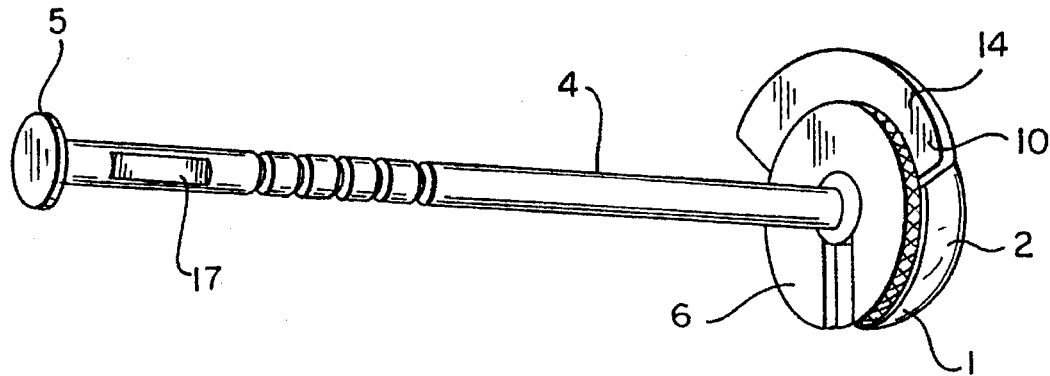

ACETABULAR BONE GRAFT IMPACTOR

BACKGROUND OF THE INVENTION

1. Field of the Invention

This invention relates to an acetabular bone graft impactor. More particularly it relates to instruments that are used to reconstruct the acetabular cavity with morselised bone graft to repair bone defects.

2. Description of the Prior Art

The technique of morselised bone grafting has been used for the reconstruction of bone defects in bones as well as in the acetabular cavity using simple basic instruments such as impactors. The shape of these impactors is usually hemispherical and used with a hammer in order to impact the bone graft in place to fill bone defects.

Acetabular impactors, as presently used, usually have a shape that is generally similar to the shape of a healthy acetabulum. The most common defects are all around the acetabular cavity, known as the rim. Therefore, the strongest impaction is performed in the areas where there are no defects and no requirements for strong impaction. Due to a lack of bone support and perpendicular impaction to the opening of the cavity, the area where the strongest impaction is required is often only very weakly or not impacted at all. The can lead to a failure of the surgical procedure such as migration of the prosthetic component, resorbtion of the graft.

When performing the operation it is also possible to see the graft issuing out of the cavity during the impaction. This induces a waste of expensive bone graft, particularly in the area of the opening of the defect.

SUMMARY OF THE INVENTION

It is an object of the present invention to provide the surgeon with an acetabular impactor that will avoid the above-mentioned problems by giving the surgeon the ability to impact the graft in the area of the defect he wants to fill. As the acetabular rim defects can have various shapes, the impactor is adaptable as required.

According to the present invention an acetabular bone graft impactor comprises a head having a contract surface and which is connected to a shaft provided with an anvil, and a device is provided for altering the shape of the contact surface.

In a preferred embodiment the device for altering the shape of the contact surface can have a releasable connection for attachment to the shaft and/or the head. The device for altering the shape of the contact surface can include a flange which, when the means are in place, projects radially outwardly beyond the contract surface of the head. Such a flange is preferably a sector of a circle.

In an alternative construction the device for altering the shape of the contact surface can be permanently attached to a second shaft and the head is removable form the first shaft and can be transferred to the second shaft to alter the shape of the contact surface.

These and other objects and advantages of the present invention will become apparent from the following description of the accompanying drawings, which disclose several embodiments of the invention. It is to be understood that the drawings are to be used for the purposes of illustration only and not as a definition of the invention.

BRIEF DESCRIPTION OF THE DRAWINGS

In the drawings, wherein similar reference characters denote similar elements throughout the several views:

FIG. 1 is an exploded isometric view of the components of the acetabular bone graft impactor according to the invention;

FIG. 2 is an isometric view of the impact components shown in FIG. 1 in their assembled positions;

DESCRIPTION OF THE PREFERRED EMBODIMENT

Figure 3:
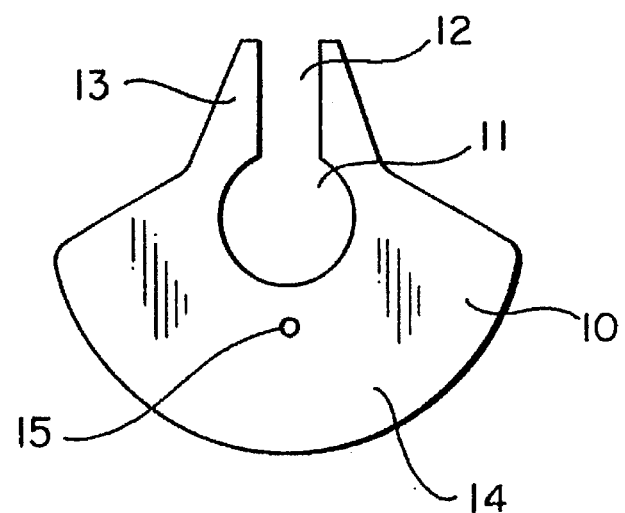
FIG. 3 is a plan view of the attachable device for altering the shape of the contract surface of the construction shown in FIG. 1 and FIG. 2.
Figure 4:
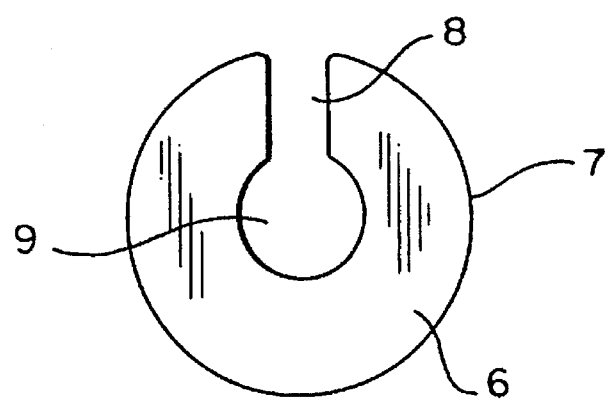
FIG. 4 is a plan view of a locking nut used in the construction shown in FIG. 1 and FIG. 2.

Referring to the drawings, the preferred acetabular bone graft impactor of the present invention comprises a metal or hard material head 1 which is of hemispherical shape and which has a contract surface 2 and a rear face 3. The head 1 is carried on a shaft 4 the other end of which is provided with an anvil 5a. Thus, the impactor so far described is generally of known form.

In order to provide attachable devices for altering the shape of contact surface 2, shaft 4 is provided with a screw thread 5 at its end adjacent rear face 3 of the head. Screw thread 5 is adapted to take a nut 6 which has a knurled rim 7. Nut 6 is also provided with a slot 8 leading from its outer rim 7 to a screw threaded opening 9.

The attachable device itself is provided by a flange element 10 which has an opening 11 leads to a slot 12 in an extension 13. The remainder of the flange element 10 is formed by a flange 14 preferably in the form of a sector of a circle and in which is a location opening or hole 15.

The rear face 3 of head 1 is provided with a location boss or stud 16 and shaft 4 carries flats 17 the width across which is slightly less than the width across the faces of slot 8 in the nut 6 and slot 12 in flange element 10.

In order to assemble the attachable device flange element 10 is located on shaft 4 by sliding slot 12 over flats 17 and then moving the element down the shaft until opening 11 surrounds the screw thread 5. It will be appreciated that due to the keyhole shape of opening 11 and slot 12 the element 10 cannot be detached and it is located in a given angular position by engagement of location opening 15 over location boss 16 on rear face 3 of head 1.

Nut 6 is now placed in position in a similar manner and so that its screw threaded opening 9 can engage screw thread 5 and the outer surface of flange element 10. Rotation of the nut can be sufficient to hold flange element 10 firmly in position.

Referring to FIG. 2 there is shown the assembled impactor with flange 14 of flange element 10 projecting radially outwardly from the head. The lower surface 17 of flange 14 now acts to extend contact surface of head 1 thus altering the shape of the total contact surface.

Flange element 10 can be made slightly flexible, for example by making it from a medical grade plastics material. Thus, flange 10 can be customized in the operating theatre using convention pliers or scissors. Being adaptable, once it has been customized, nor not, it can be used with all sizes of impactors having, for example, different shaped heads 1 provided shaft 4 or flats 17 and screw thread 5 are the same.

The shape of the flange fulfills two main requirements, the first for impacting the graft and the second for attachment to the impactors. The impaction of the graft is performed by the transmission of forces via the impactor to the flange and ultimately the graft. Thus anvil 5a is struck appropriately by either an impact hammer or some other device.

It will be appreciated that the impactor can be used without the attachable device for altering the shape of the contact surface. Thus it can be used in the configuration shown in FIG. 1 without fittings 6 and 10. It is therefore possible to insert and disengage the attachable device, for example at the final stage of the fixing process.

In addition, various size and shape flanges 10 can be used alone or in series to vary the shape of the bone graft contact surface. Flange 10 can also be made from a heavier material if desired and if so it can be pre-shaped as required. The effect of flange 10 is to enable the outer perimeter of the acetabular socket to be compacted and prevent the problems referred to above.

Figure 5:
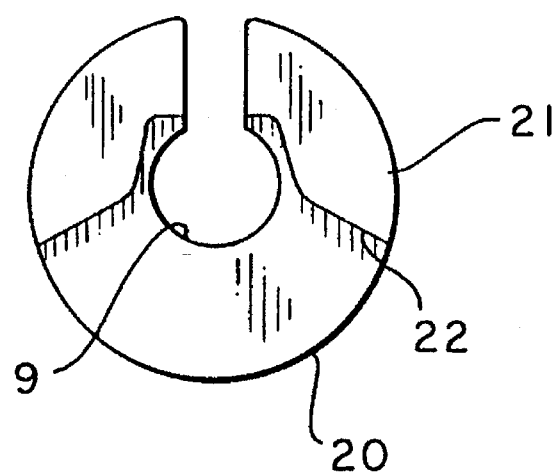
FIG. 5 is a plan view of an alternative construction of locking nut.
Figure 6:
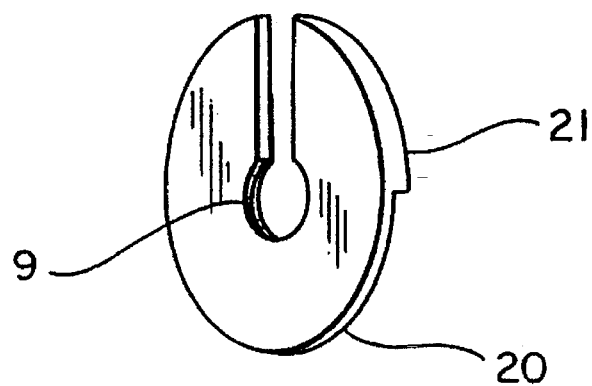
FIG. 6 is an isometric view of the locking nut shown in FIG. 5.

FIG. 5 shows an alternative construction of locking nut 20 which can be used with a flange element 10 of the kind shown in FIG. 3. In this construction the engaging face 21 of the lock nut 20 is cut away at 22 to form a shape similar to the shape of the outer perimeter of the engaging part of the flange element 10. As will be seen from FIG. 6 the cut away 22 is of substantially the same depth as the thickness of the flange element 10 so that the appropriate portions of the flange element and the lock nut can nest together. With this construction the location of boss 6 on the rear face 3 of the head 1 is omitted but the locking nut 20 enables the flange element 10 to be held firmly against the face 3 of the head when the lock nut is screwed down into position on the thread 5 thereby preventing any selective rotation between the two plates.

Figure 7:
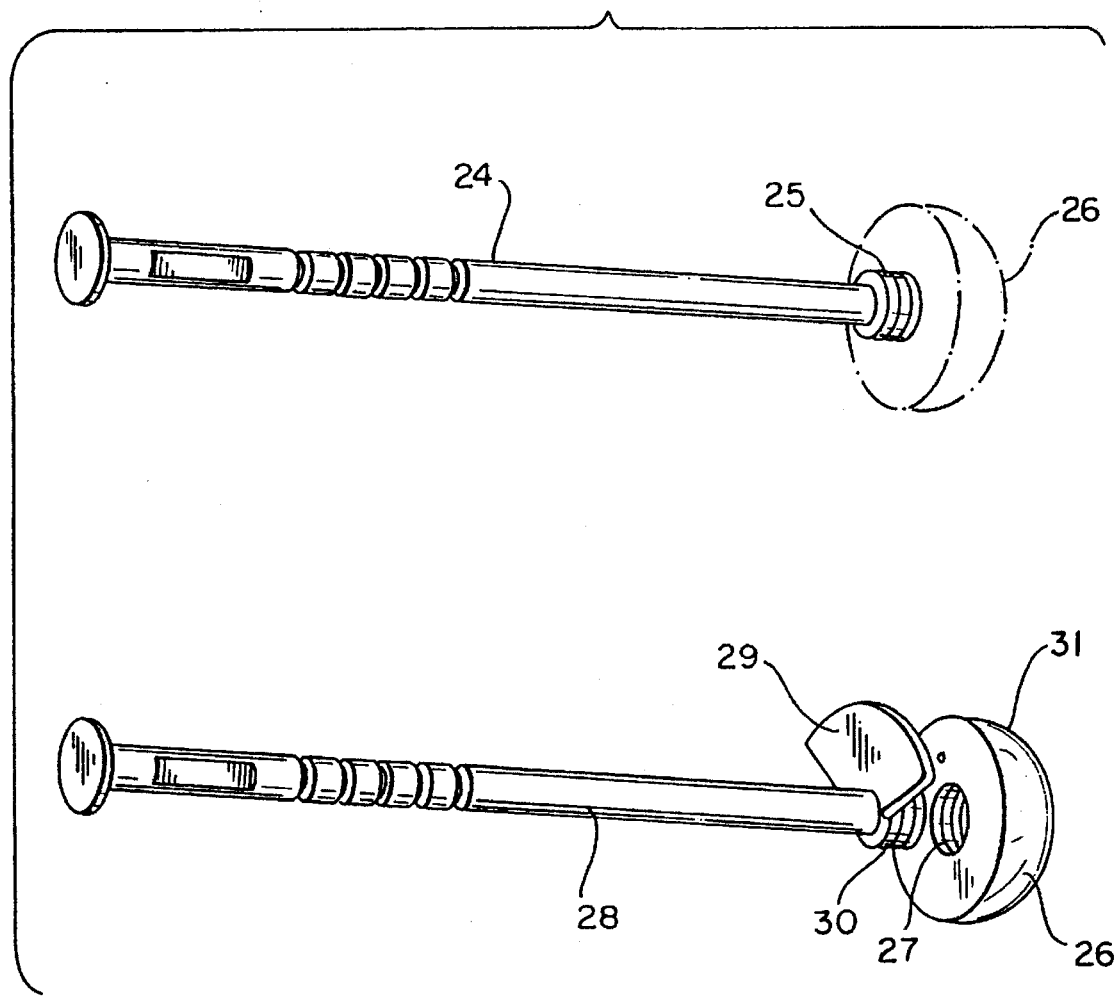
FIG. 7 is an exploded isometric view of a further alternative construction according to the invention.

FIG. 7 shows an alternative construction in which the shaft 24 is of similar construction to the shaft 4 described in the preferred embodiment shown in FIG. 1 but in which the end of the shaft carries a screw thread 25 to receive a hemi-spherical head 26 which is provided with a screw threaded bore 27 so that the head 26 can be screwed onto the shaft 24. The head is shown in this position in phantom at the upper part of the Figure.

A second shaft 28 is provided to which is rigidly connection a flange element 29 immediately above a screw threaded end 30 the dimension of which are similar to the screw threaded end 25 on the shaft 24.

When the first impaction has been completed the detachable head 26 can be removed from the stem 24 and attached by means of the screw thread 30 to the shaft 28, the flange element 10 thus acting to extend the contact surface 31 of the head 26 which therefore alters the shape of the total contact surface.

Once again the effect of the flange 29 is to enable the outer perimeter of the acetabular socket to be compacted to prevent the problems referred to above.

I claim:

1. An acetabular bone graft impactor comprising a shaft having an anvil at one end and a head at a second end, a contact surface at least part of which is located on said head and, a flange releasably connected to said second end of said shaft forming at least part of said contact surface, wherein the flange is connected to the head and projects radially outwardly from the contact surface thereon; and in which said flange is a sector of a circle.

2. An acetabular bone graft impactor comprising a shaft having an anvil at one end and a head at a second end, a contact surface at least part of which is located on said head and, a flange releasably connected to said second end of said shaft forming at least part of said contact surface, said acetabular bone graft impactor including a second shaft provided with an anvil and to which the flange for altering the shape of the contact surface is attached, said second shaft having means to receive the head of said first shaft and to which the head can be transferred to alter the shape of the contact surface, said means for altering the shape of the contact surface includes a flange attached to said second shaft which projects radially outwardly beyond the contract surface on the head when in position on the second shaft to alter the shape of the total contact surface, said flange being a sector of a circle.

* * * * *